(12) United States Patent
Nasr

(10) Patent No.: US 12,290,298 B2
(45) Date of Patent: *May 6, 2025

(54) AUTOLOADING SCREWDRIVER APPARATUS

(71) Applicant: Bio Med Pro LLC, Mission Viejo, CA (US)

(72) Inventor: Michael Nasr, Mission Viejo, CA (US)

(73) Assignee: BIO MED PRO LLC, Mission Viejo, CA (US)

( * ) Notice: Subject to any disclaimer, the term of this patent is extended or adjusted under 35 U.S.C. 154(b) by 145 days.

This patent is subject to a terminal disclaimer.

(21) Appl. No.: 17/728,772

(22) Filed: Apr. 25, 2022

(65) Prior Publication Data

US 2023/0165614 A1 Jun. 1, 2023

Related U.S. Application Data

(63) Continuation of application No. 17/539,015, filed on Nov. 30, 2021, now Pat. No. 11,337,743.

(51) Int. Cl.
*A61B 17/88* (2006.01)
*A61B 17/86* (2006.01)
*B25B 23/06* (2006.01)

(52) U.S. Cl.
CPC ........ *A61B 17/8875* (2013.01); *A61B 17/865* (2013.01); *B25B 23/06* (2013.01)

(58) Field of Classification Search
CPC . A61B 17/865; A61B 17/8875; B25B 23/045; B25B 23/06
See application file for complete search history.

(56) References Cited

U.S. PATENT DOCUMENTS

| 4,442,738 | A | 4/1984 | Spencer |
| 4,998,452 | A | 3/1991 | Blum |
| 6,502,484 | B2 | 1/2003 | Pao-Hsi |
| 6,510,768 | B2 | 1/2003 | Frühm |
| 6,813,977 | B2 * | 11/2004 | Goodhue ................ B25B 23/06 |
| | | | 81/433 |
| 7,188,555 | B2 | 3/2007 | Beauchamp |
| 8,087,325 | B2 | 1/2012 | Neubardt |
| 8,534,164 | B2 | 9/2013 | Watt |
| 9,271,732 | B2 * | 3/2016 | Walker .................. A61B 17/10 |
| 10,433,882 | B2 | 10/2019 | O'Neil et al. |
| 10,820,911 | B2 | 11/2020 | Delman et al. |

(Continued)

*Primary Examiner* — Larry E Waggle, Jr.
(74) *Attorney, Agent, or Firm* — Seed IP Law Group LLP

(57) ABSTRACT

An autoloading screwdriver apparatus is provided which includes a base; a screw cartridge received by the base; a driver supported within the base that is selectively engageable with a screw of the screw cartridge by manually displacing the driver toward a working end of the autoloading screwdriver apparatus; and a handle grip movably coupled to the base and configured to be manually displaced in a longitudinal direction toward the working end of the autoloading screwdriver apparatus to move the driver into engagement with the screw and to displace the screw to the working end of the autoloading screwdriver apparatus for presenting the screw to be screwed into a target substrate. The autoloading screwdriver apparatus may further include a control element manipulable by a user to activate rotational movement of the driver to drive the screw into the target substrate.

19 Claims, 6 Drawing Sheets

(56) References Cited

U.S. PATENT DOCUMENTS

| | | |
|---|---|---|
| 11,065,745 B2 | 7/2021 | Garcia et al. |
| 11,337,743 B1 * | 5/2022 | Nasr .................... A61B 17/865 |
| 2007/0245862 A1 * | 10/2007 | Gonzalez ............... B25G 1/085 |
| | | 81/439 |
| 2020/0009710 A1 * | 1/2020 | Bethoux ............ A61B 17/7091 |

* cited by examiner

AUTOLOADING SCREWDRIVER APPARATUS

CROSS-REFERENCE TO RELATED APPLICATIONS

This application is a continuation of U.S. patent application Ser. No. 17/539,015, filed Nov. 30, 2021, the content of which is hereby incorporated by reference in its entirety.

BACKGROUND

Technical Field

The present disclosure relates generally to screwdrivers and, more specifically, to autoloading screwdrivers that allow a user to load screws on a driver thereof without having to manually place or hold a screw on the driver head or rely on pretensioned screw holding cartridges or complex electronic control systems. Such autoloading screwdrivers may be particularly well suited for installing screws in surgical applications.

Description of the Related Art

In a number of applications, a person wishing to place screws into a material must manually place screws at the head of a screwdriver and hold the screw in place against a material to receive the screw and against the screwdriver. Some screwdrivers are made of ferromagnetic material, so that when using a screw made of material attracted to magnetic materials, the screw generally will remain attached to the screwdriver. A problem with this type of screwdriver is when the screw is not ferromagnetic, like titanium screws in a medical application, the magnetic material will not hold the screws using magnetic force. Other screwdrivers have very tight tolerances relative to specific screws for which they are used, so that the screws tends to remain in place on the screwdriver due to the mechanical force (friction) of the driver head on the screw's head (the screw is effectively wedged onto the screwdriver head and, due to the tight tolerance, the screw clasps the screwdriver head reducing the likelihood the screw will separate from the screwdriver before attaching to the material to receive the screw). This mechanical solution may be helpful even when the magnetic screwdriver/magnetic screw solution is available, but is even more useful when screws are non-magnetic. A problem with this type of screwdriver is fixing the screw on the screwdriver head at the beginning and the possibility of dropping the screw if the screw becomes detached from the screwdriver head because the friction is insufficient to keep the screw in place.

In many instances where screws are large relative to the fingers of the user, manually loading the screw on the screwdriver head does not pose a significant challenge to the user. However, for repeated, manual applications of the same screw sizes to a screw application job, this manual placement is not convenient and requires careful coordination of the screw to the materials and to the screwdriver to ensure the screw is applied to the right area of the material and at the right angle, typically perpendicular to the material to receive the screw.

However, the inconvenience and level of coordination increases significantly when the screws become smaller relative to the fingers of the user. This might be the case when repairing eyeglass frames for example. It is also the case for orthopedic and neurosurgery applications, where very small, non-magnetic, titanium screws are often used to fasten plates to join bone during healing.

Using neurosurgery to provide further background on the problem, using conventional orthopedic screwdrivers, surgeons currently are required to take tiny screws (typically about 1 mm in diameter and 4 mm in length) from a box and move them to the scalp, find the right spot on the bone joining plate—a very tiny hole usually 1 mm in diameter—and tighten the screw into the skull of the affected cranial area. Since the screws are typically made of titanium (non-magnetic), it is not possible to use magnetic screwdrivers. Therefore, the screwdriver and the screw-head tolerance must be very tight to increase the mechanical bond between the screw and the screwdriver to reduce the likelihood that the screw will separate from the screwdriver prior to insertion into the bone. This requirement for tight tolerances not only increases the cost of manufacturing the screws and screwdrivers, but also makes picking up and handling the screws very difficult and risky (since the mechanical bond may be insufficient). The tight mechanical bond does not prevent dropping the expensive, tiny screws. It only reduces the chance of such a separation.

Conventional electric screwdrivers help surgeons to drive the screw into place, but have the additional risk of spinning off the screws and flinging them around to where they cannot be seen easily due to their tiny size. These tiny screws can end up in the patient's open wound, which could be disastrous if the screws remain there after the operation is completed. An advantage of the electrical screwdrivers over the manual ones is the ease of driving the screws into the bone.

Time is also very critical during neurosurgery. It can save the patient's life. Therefore, another problem with the manual loading process is that it is very time consuming. Neurosurgeons experience additional time lost and frustration due to screw drops. As a result, use of conventional screwdrivers for neurosurgeons has drawbacks and shortcomings.

Some examples of known screwdrivers include those shown and described in U.S. Patent Pub. No. 2020/0009710 to Bethoux et al., U.S. Pat. No. 9,271,732 to Walker, and U.S. Pat. No. 10,433,882 to O'Neil et al.

Thus, while an operator today has several alternatives for loading and applying screws, each has limitations.

BRIEF SUMMARY

The autoloading screwdriver apparatuses, removable screw and tool cartridges thereof and other components and related methods shown and described herein provide autoloading screwdriver form factors that are robust, efficient, and particularly effective at driving screws with precision and reduced risk of undesirable separation of the screws from a driver thereof. Embodiments enable a user to avoid manually loading screws at the end of a driver and enable the user to displace screws from a loaded screw cartridge to a target site with relative ease.

According to one embodiment, an autoloading screwdriver apparatus may be summarized as including a base; a screw cartridge received by the base and including a plurality of screws to be discharged from the screwdriver apparatus; a driver supported within the base and selectively engageable with one of the plurality of screws of the screw cartridge by manually displacing the driver toward a working end of the screwdriver apparatus; and a handle grip movably coupled to the base and configured to be manually displaced in a longitudinal direction by a user toward the working end of the screwdriver apparatus to move the driver into engagement with one of the plurality of screws and to displace the screw to the working end of the screwdriver apparatus for presenting the screw to be screwed into a target substrate. The screwdriver apparatus may further include a control element manipulable by a user to activate rotational movement of the driver to drive the screw into the target substrate. Notably, the displacement of the handle grip, the driver and the screw toward the working end of the screwdriver apparatus may be carried out independent of manipulation of the control element to activate rotational movement of the driver. In some instances, the control element may be carried by the handle grip for manipulation by the user on the handle grip.

Advantageously, the screw cartridge may be removably received by the base to enable the screw cartridge to be selectively replaced with a replacement screw cartridge.

The handle grip may include a screw cartridge driver that is arranged to interact with the screw cartridge to advance the screw cartridge to a next one of a plurality of incremental rotational positions as the handle grip is displaced fore and aft during use. The screw cartridge driver may be configured to interact with indexing structures on an outer circumferential portion of the screw cartridge to advance the screw cartridge to the next one of the plurality of incremental rotational positions as the handle grip is displaced fore and aft during use. The indexing structures on the outer circumferential portion of the screw cartridge may comprise an array of sets of intersecting channels, wherein each set of intersecting channels in the array includes a longitudinal channel of varying depth and an oblique channel extending from a leading end of the screw cartridge to a mid-section of the longitudinal channel, and whereby, during advancement of the handle grip to a forward position, an indexing structure of the screw cartridge driver extends beyond a terminal end of the longitudinal channel of one of the sets of intersecting channels in the array and enters the oblique channel of an adjacent one of the sets of intersecting channels, and, during retraction of the handle grip to an aft position, the indexing structure of the screw cartridge driver rides in the oblique channel and drives rotation of the screw cartridge to the next one of the plurality of incremental rotational positions. The indexing structure of the screw cartridge driver may comprise a plunger, such as a spring and/or magnetically biased plunger, that extends radially inward toward a central rotational axis of the screw cartridge.

The screw cartridge may include a screw cartridge cap including a plurality of screw receiving apertures in which the plurality of screws are receiveably held, a screw cartridge body having a plurality of screw passages through each of which a respective one of the screws is positioned, and an axial plunger assembly configured to enable the screw cartridge to be removably received by the base of the screwdriver apparatus.

The screwdriver apparatus may further include a drive motor and a plurality of mechanical power transmission components coupled between the drive motor and the driver to transfer rotational motion of the drive motor to the driver during use. The plurality of mechanical power transmission components may include a driver gear coupled to an output of the drive motor, a pinion gear coupled to the driver, and an intermediate gear meshed with both of the driver gear and the pinion gear. The intermediate gear may include elongated teeth enabling the pinion gear to slide longitudinally back and forth along a length of the intermediate gear during displacement of the handle grip and driver during use of the screwdriver apparatus. The plurality of mechanical power transmission components may further include a torque transmission coupling or clutch positioned between the drive motor and the driver gear that is configured to limit an amount of output torque that can be delivered to the driver by the drive motor.

The screwdriver apparatus may further include a control system configured to selectively control an amount of output torque and/or a drive speed of the driver provided by the screwdriver apparatus. The screwdriver apparatus may further include a display to display the amount of output torque and/or the drive speed of the driver provided by the screwdriver apparatus and/or other data such as battery charge level.

The driver may be part of a driver assembly, and the driver assembly may include a return spring to bias the driver toward an aft position to enable the driver to return from an advanced position to the aft position under the bias of the return spring. The handle grip may be displaceable toward the working end by manually overcoming the bias of the return spring. The bias of the return spring may assist in rotating the screw cartridge to a next one of a plurality of incremental rotational positions as the driver retreats to the aft position to position another screw in working alignment with the driver. The driver assembly may be coupled to the handle grip to move longitudinally in unison therewith, and the driver may be supported by a rotational bearing fixedly coupled to the handle grip to enable the driver to rotate about a longitudinal driver axis upon manipulation of the control element by the user.

The screwdriver apparatus may further include a disposable screw holder bushing removably coupled to the working end of the screwdriver apparatus and including a screw passageway sized correspondingly to the screws of the screw cartridge.

The base of the screwdriver apparatus may include a screw cartridge-receiving cavity on a lower side thereof for insertably receiving the screw cartridge. The screw cartridge may include one or more indicators on a side thereof to facilitate loading in proper working alignment when inserted in the screw cartridge-receiving cavity.

Advantageously, the screwdriver apparatus may be configured to be equipped with a different type and/or a size of drivers or tools. For example, the screwdriver apparatus may further include a driver cartridge received by the base and accommodating a plurality of drivers or other tools (e.g., drill bit) selectable by the user by rotating the driver cartridge relative to the base to position a desired one of the plurality of drivers into an active position. The driver in the active position may be engageable by a driver assembly that is coupled to the handle grip to move longitudinally in unison therewith. The base may include a driver cartridge-receiving cavity on a lower side thereof for insertably receiving the driver cartridge.

DETAILED DESCRIPTION

In the following description, certain specific details are set forth in order to provide a thorough understanding of various disclosed embodiments. However, one skilled in the relevant art will recognize that embodiments may be practiced without one or more of these specific details. In other instances, well-known devices, structures and techniques associated with screwdrivers, components thereof and related methods of driving screws may not be shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

With reference to FIGS. 1 through 4, the present disclosure relates generally to screwdrivers and, more specifically, to autoloading screwdrivers that allow a user to load screws on a driver thereof without having to manually place or hold a screw on the driver head or rely on pretensioned screw holding cartridges or complex electronic control systems. The autoloading screwdrivers disclosed herein may be particularly well suited for driving screws in surgical applications.

Figure 1:
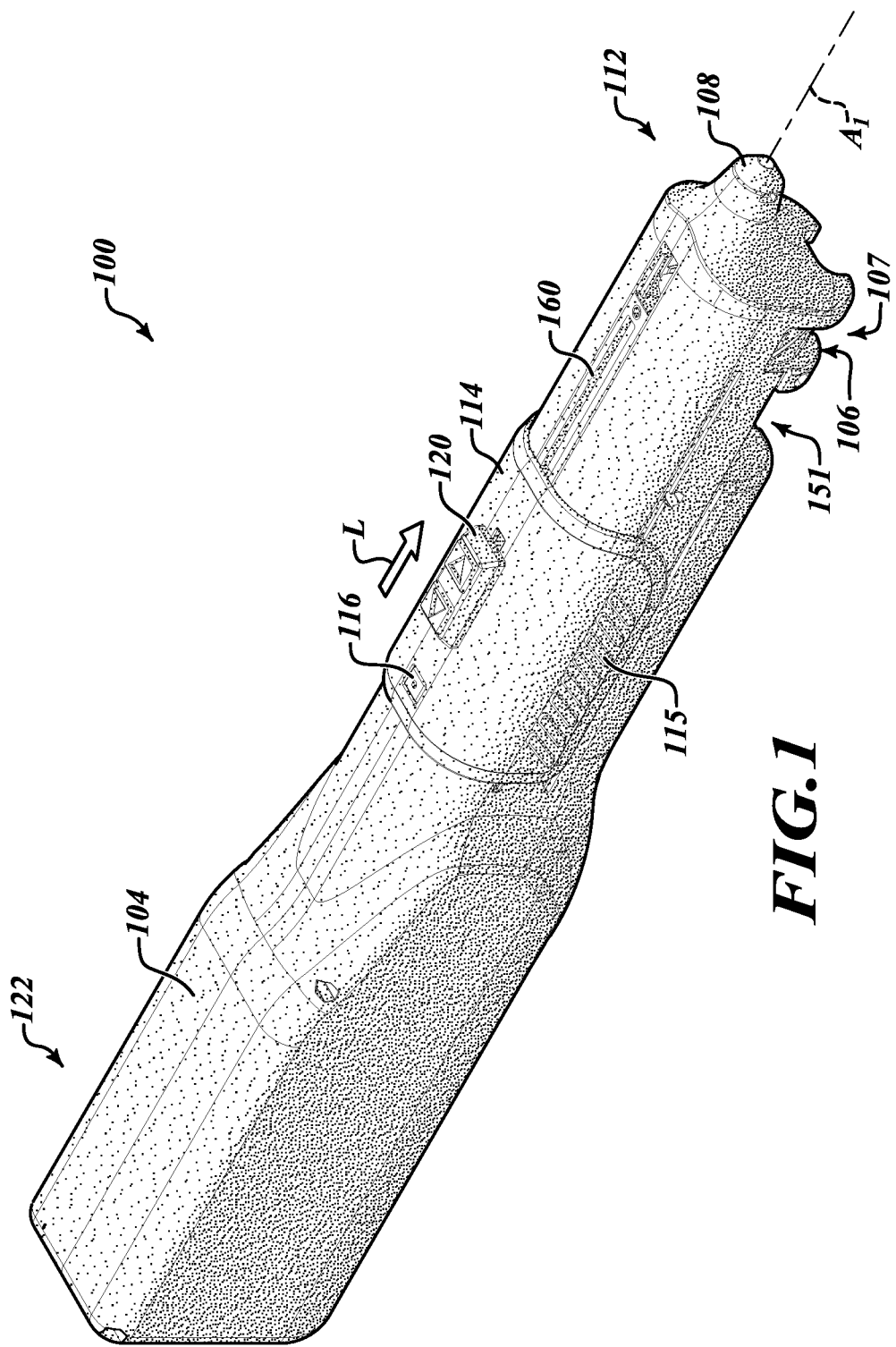
FIG. 1 is a perspective view of an autoloading screwdriver apparatus, according to an example embodiment, which is particularly well adapted to serve as a multi-use (universal) screwdriver.
Figure 2:
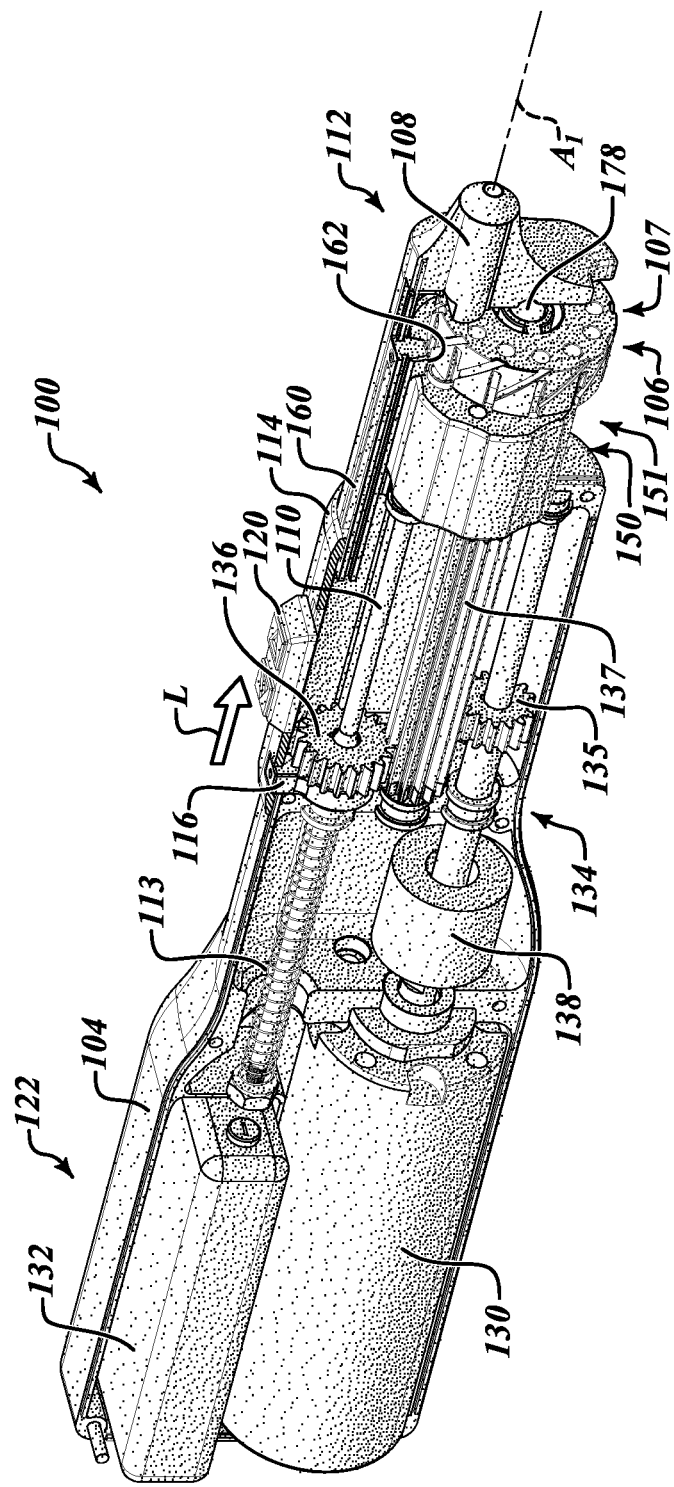
FIG. 2 is a perspective view of the autoloading screwdriver apparatus of FIG. 1 with half of a housing or base and half of a handle grip thereof removed to reveal internal components.
Figure 3:
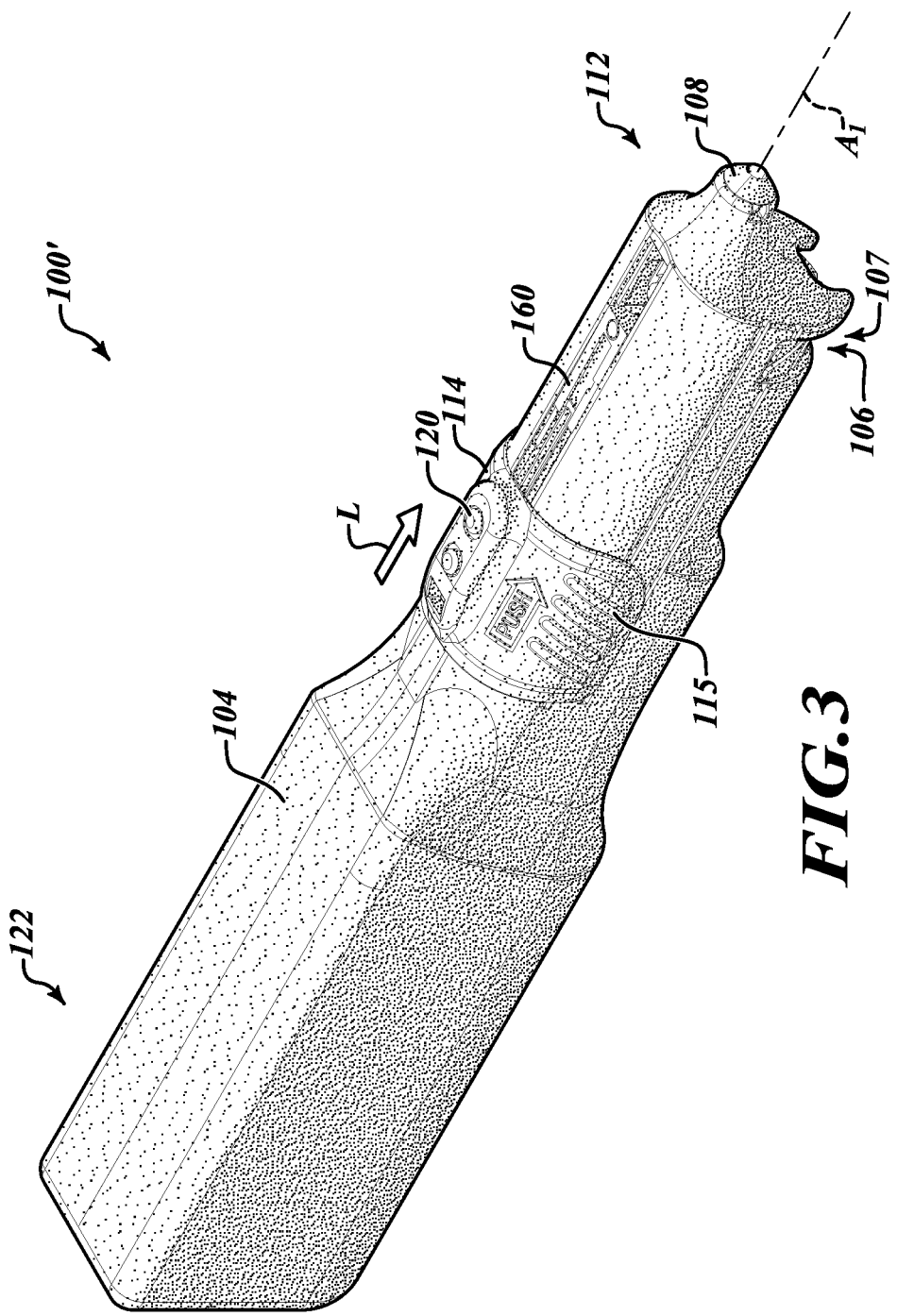
FIG. 3 is a perspective view of an autoloading screwdriver apparatus, according to another example embodiment, which is particularly well adapted to serve as a disposable, single use screwdriver.

As shown in FIGS. 1 through 4, autoloading screwdriver apparatuses 100, 100' of the present disclosure may be provided in form factors that are particularly well adapted to present screws 102 (FIGS. 5 and 6) to a surgical or other target site in a repeatable and reliable manner with little to no risk of inadvertent loss of the screws 102. The embodiment illustrated in FIGS. 1 and 2 is directed to an autoloading screwdriver apparatus 100 that is similar in function and features to the embodiment of the autoloading screwdriver apparatus 100' illustrated in FIGS. 3 and 4, but includes, among other things, the additional aspect of a tool cartridge 150 for enabling a user to select from among a variety of different tools (e.g., different driver types and sizes) for use in driving screws into a target substrate during, for example, a surgical procedure. Accordingly, like elements among the illustrated embodiments will be labeled with the same reference characters in the drawings for clarity.

With reference to FIGS. 1 through 4, example embodiments of autoloading screwdriver apparatuses 100, 100' are shown having a housing or base 104 and a screw cartridge 106 that is insertably received by the housing or base 104. The screw cartridge 106 includes a plurality of screws 102 (FIGS. 5 and 6) to be discharged from the screwdriver apparatuses 100, 100' and may be removably received by the housing or base 104 to enable the screw cartridge 106 to be selectively replaced with a replacement screw cartridge 106 as needed or desired. The apparatuses 100, 100' further include a driver or driver shaft (hereinafter collectively referred to as driver 110) supported within the housing or base 104, which is selectively engageable (either directly or indirectly) with one of the plurality of screws 102 of the screw cartridge 106 by manually displacing the driver 110 toward a working end 112 of the apparatuses 100, 100'.

The screwdriver apparatuses 100, 100' further include a handle grip 114 movably coupled to the housing or base 104, which is configured to be manually displaced in a longitudinal direction L by a user toward the working end 112 of the screwdriver apparatuses 100, 100' to move the driver 110 into engagement with one of the plurality of screws 102 and to displace the screw 102 to the working end 112 of the screwdriver apparatuses 100, 100' for presenting the screw 102 to be driven into a target substrate (not shown).

The screwdriver apparatuses 100, 100' may further include a control element 120 (e.g., control switches, control buttons) manipulable by a user to activate rotational movement of the driver 110 to drive the screw into the target substrate. Notably, the displacement of the handle grip 114, the driver 110 and the screw 102 toward the working end 112 of the screwdriver apparatuses 100, 100' may be carried out independent of manipulation of the control element 120 to activate rotational movement of the driver 110.

A base end 122 of the screwdriver apparatuses 100, 100' may rest comfortably on or within the user's hand while allowing the user to displace the handle grip 114 toward the working end 112 by moving the handle grip 114 relative to housing or base 104 with the user's fingertips to move the driver 110 into engagement with the screw 102 and thereafter to position the screw 102 at the working end 112, thus enabling one-handed operation. One of the user's fingertips (e.g. pointer fingertip) may then conveniently operate the control element 120 to activate rotational movement of the driver 110 to drive the screw 102 into the target substrate. Although the control element 120 is advantageously shown carried by the handle grip 114 for manipulation by the user or operator on the handle grip 114, it is appreciated that in other embodiments the control element 120 may be located elsewhere apart from the handle grip 114.

Figure 4:
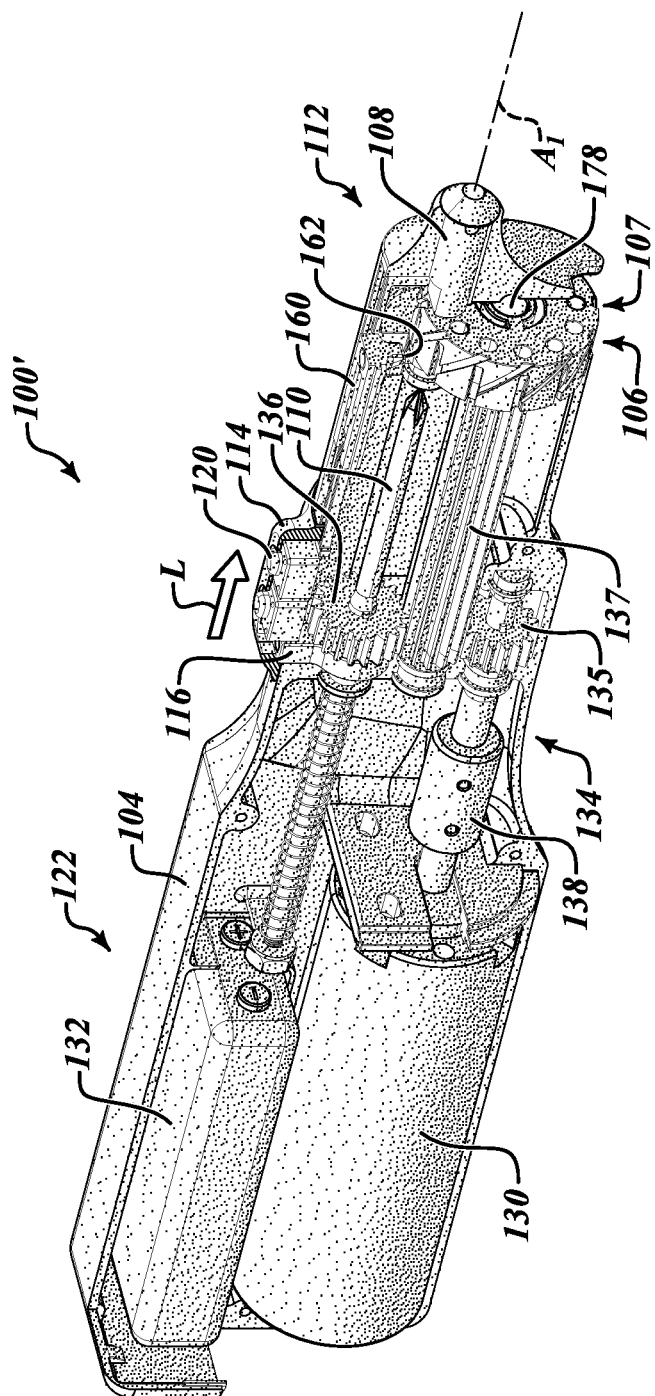
FIG. 4 is a perspective view of the autoloading screwdriver apparatus of FIG. 3 with half of a housing or base and half of a handle grip thereof removed to reveal internal components.

FIGS. 2 and 4 depict a perspective view of the embodiments of the screwdriver apparatuses 100, 100' with half of the housing or base 104 and half of the handle grip 114 thereof removed to reveal interior components. As shown in FIGS. 2 and 4, the screwdriver apparatuses 100, 100' may include a drive motor 130 (e.g., a planetary high torque electric DC gear motor); a power supply or battery 132 (e.g., lithium/manganese dioxide battery) for powering the drive motor 130; and a plurality of mechanical power transmission components 134 coupled between the drive motor 130 and the driver 110 to transfer rotational motion of the drive motor 130 to the driver 110 during use. The plurality of mechanical power transmission components 134 may include a driver gear 135 coupled to an output of the drive motor 130, a pinion gear 136 coupled to the driver 110, and an intermediate gear 137 meshed with both of the driver gear 135 and the pinion gear 136. As shown, the intermediate gear 137 may include elongated teeth enabling the pinion gear 136 to slide longitudinally back and forth along a length of the intermediate gear 137 during displacement of the handle grip 114 and driver 110 during use of the screwdriver apparatuses 100, 100'. The plurality of mechanical power transmission components 134 may further include a torque transmission coupling or clutch 138 positioned between the drive motor 130 and the driver gear 135 that is configured to limit an amount of output torque that can be delivered to the driver 110 by the drive motor 130. The torque transmission coupling or clutch 138 is configured to control torque to prevent damage to and the stalling of the drive motor 130 when a screw 102 is completely tight or the torque is exceeding, for example, a range suitable for the bone or skull of the patient.

Figure 5:
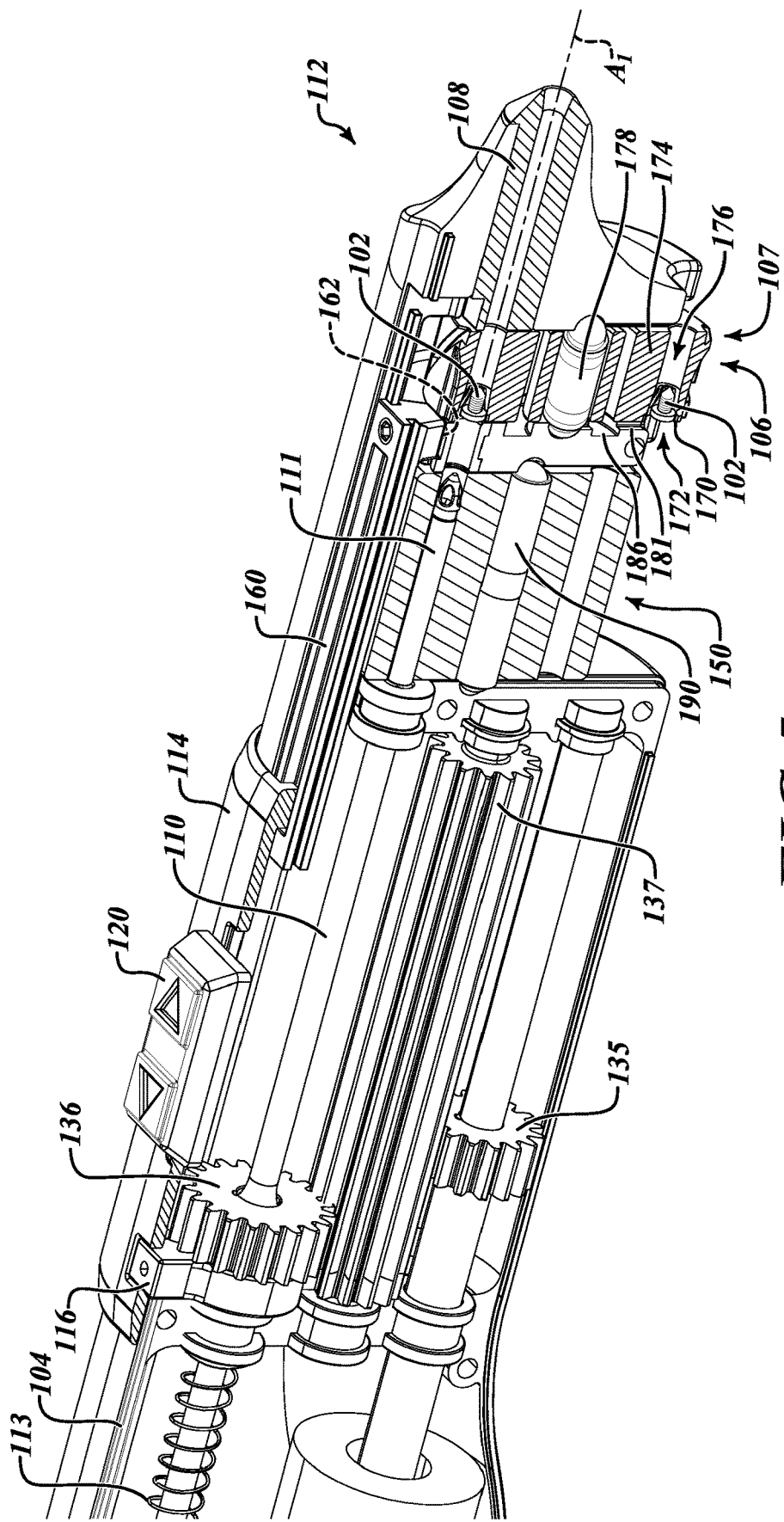
FIG. 5 is an enlarged perspective view of a working end portion of the autoloading screwdriver apparatus of FIGS. 1 and 2 with half of the housing or base removed and select components shown in cross-section to reveal additional details.

FIG. 5 provides an enlarged view of the working end 112 of the screwdriver apparatus 100 of FIGS. 1 and 2 with some of the components cutaway in cross-section to show additional details of the screwdriver apparatus 100. As can be appreciated in a review of FIG. 5, the driver 110 and pinion gear 136 fixed thereto may be moved distally along the intermediate gear 137 during use by the action of the operator on the handle grip 114. The handle grip 114 is attached to the driver 110 by a loading handle 116. As the handle grip 114 and loading handle 116 is moved distally, the driver 110 is displaced and engages with a tool 111 selected by the operator, which then engages with a screw 102 in the screw cartridge 106 and pushes it through a removable screw holder bushing 108 positioned at the working end 112 of the screwdriver apparatus 100. The removable screw holder bushing 108 may be provided to assist in preventing screws 102 from falling from the working end 112 of the screwdriver apparatus 100, 100'.

With continued reference to FIG. 5, the driver 110 may be part of a driver assembly, and the driver assembly may include a return spring 113 that is configured to bias the driver 110 toward an aft position to enable the driver 110 to return from an advanced position to the aft position under the bias of the return spring 113. Notably, the handle grip 114 is displaceable toward the working end 112 by manually overcoming the bias of the return spring 113. The return spring 113 is compressed as the handle grip 114 is displaced toward the working end 112. Once the operator completes insertion of the screw 102 (or completes a drilling procedure, as described later), relaxation of the return spring 113 assists with the retraction of the driver 110 back to its original proximal location, as shown in FIG. 5.

With continued reference to FIG. 5, the screwdriver apparatus 100 includes a tool cartridge 150 in the form of a rotatable circular disk that is configured to hold a plurality of tools 111 therein. In this manner, the tool cartridge 150 acts as a bank of tools. When the operator wants to change a tool for use, in the case of using a different type or size of screw 102, the operator can simply rotate the tool cartridge 150 to a new tool position to select a desired one of the tools 111 before use. The tool cartridge 150 may include an axial plunger assembly 190 configured to enable the tool cartridge 150 to be removably received by the housing or base 104 of the screwdriver apparatus 100. The axial plunger assembly 190 of the tool cartridge 150 may comprise, for example, opposing ball detents to enable the tool cartridge 150 to snap into place within a tool cartridge-receiving cavity 151 (FIGS. 1, 2 and 5) and assist in precisely aligning tool passages thereof with an axis Ai of the driver 110. To maintain axial alignment between the tool cartridge 150 and the driver 110, the axial plunger assembly 190 of the tool cartridge 150 is set in the center of the tool cartridge 150. This maintains axial alignment by putting the tool cartridge 150 in the exact position to rotate with the tool passages thereof aligned precisely with the axis Ai of the driver 110.

Figure 6:
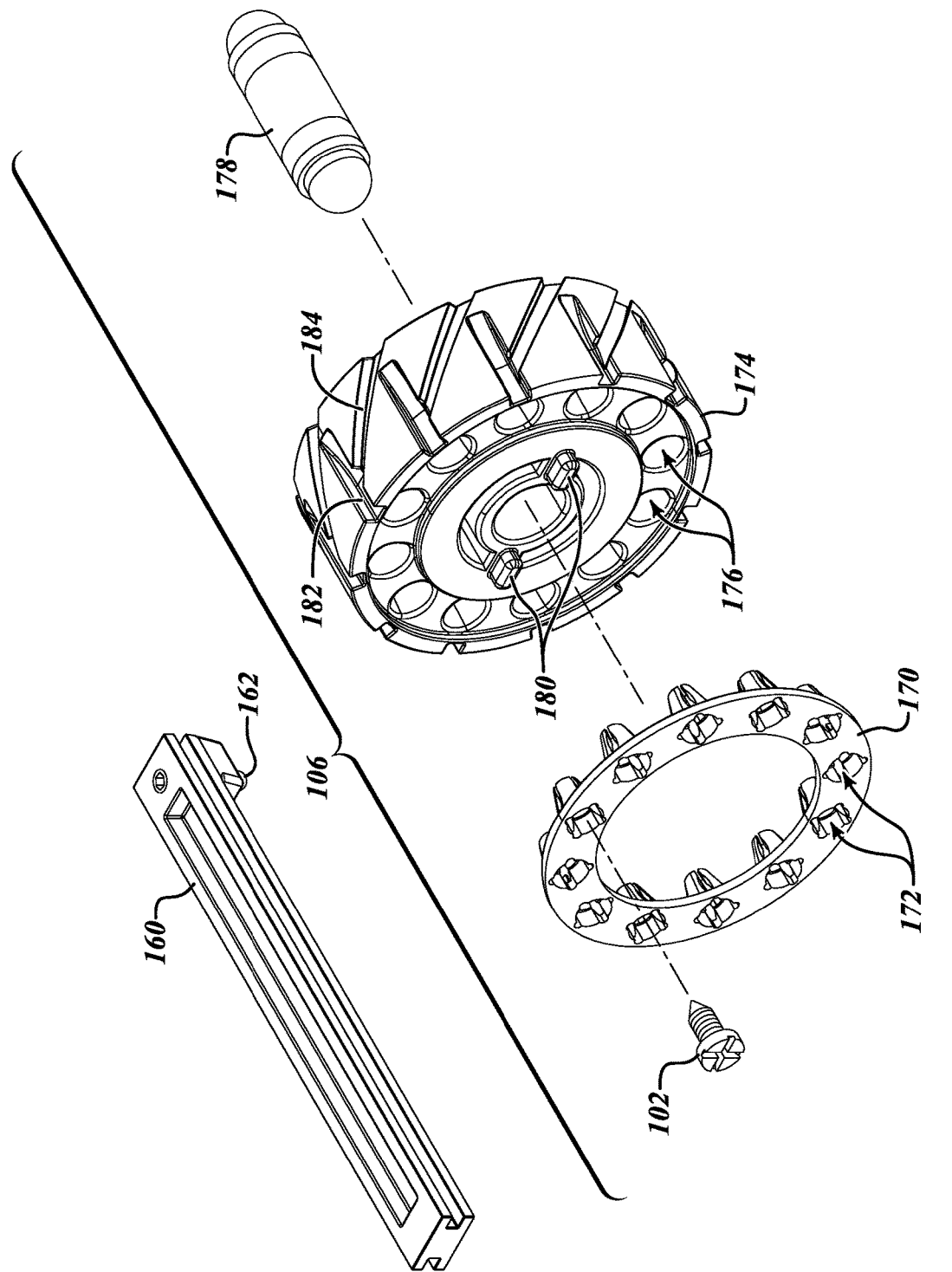
FIG. 6 is an exploded perspective view of a removable screw cartridge, according to an example embodiment, which is usable with the autoloading screwdriver apparatuses disclosed herein, along with a screw cartridge driver that is arranged to interact with the screw cartridge during use to advance the screw cartridge to a next one of a plurality of incremental rotational positions.

With reference now to FIG. 6, the screw cartridge 106 banks a plurality of screws 102 inside the screwdriver apparatus 100, 100'. The screw cartridge 106 is a kind of magazine of screws 102 that holds the screws 102 in a circular pattern or array. Based on the screw size and type, the number of screws in the screw cartridge 106 may vary. The screw cartridge 106 may be selected by the operator from a selection of different screw cartridges 106 based on the size and type of screw desired. To retain the screws 102, which may be particularly little, in the screw cartridge 106, the screw cartridge 106 may be provided with a screw holder cap 170 including a plurality of screw receiving apertures 172 in which the plurality of screws 102 are receiveably held, and a screw cartridge body 174 having a plurality of screw passages 176 through each of which a respective one of the screws 102 is positioned. The screw cartridge 106 may further include an axial plunger assembly 178 configured to enable the screw cartridge 106 to be removably received by the housing or base 104 of the screwdriver apparatus 100. The axial plunger assembly 178 may comprise, for example, opposing ball detents to enable the screw cartridge 106 to snap into place within a screw cartridge-receiving cavity 107 and to assist in precisely aligning the screw passages 176 and screws 102 received therein with the axis Ai of the driver 110. Further details of the screw cartridge 106 will be appreciated by those of ordinary skill in the relevant art upon a thorough review of FIG. 6.

As can be appreciated from FIG. 6, the screw holder cap 170 may be loaded with a series of screws 102 in the screw receiving apertures 172 and the screw holder cap 172 may be coupled to the screw cartridge body 174. The screw holder cap 170 may be selected by the operator from a selection of screw holder caps 170 based on the screw size and type desired. In the embodiment of FIG. 6, the screw holder cap 170 holds twelve screws 102 but it is appreciated more and fewer screws may be provided in other embodiments. The screw holder cap 170 may be a single-use part supplied in a separate sterilized package that may then be combined with the screw cartridge body 174 and the axial plunger assembly 178 and installed within the screwdriver apparatus 100, 100'.

To maintain axial and angular alignment between the screw cartridge body 174 and the driver 110, the axial plunger assembly 178 of the screw cartridge body 174 is set in the center of the screw cartridge body 174. This maintains axial alignment by putting the screw cartridge body 174 in the exact position to rotate with the screw passages 176 aligned precisely with the axis Ai of the driver 110.

The screw cartridge body 174 may further include one or more radial indicators 180 on the screw cartridge body 174 to facilitate proper angular alignment upon initial insertion of the screw cartridge 106. In some instances, the operator may be required to load the screw holder cap 170 into the screw cartridge body 174 and then load the resulting screw cartridge 106 into the housing or body 104 of the screwdriver apparatus 100, 100' with the radial indicators 180 aligned with a corresponding radial indicator slot 181 (FIG. 5) on the housing or body 104 with the screw heads (located on the proximal end of each screw 102) located on the proximal side of the screw cartridge body 174 of the screw cartridge 106. Advantageously, using the radial indicators 180 ensures the operator installs the screw cartridge 106 at the 12 o'clock position aligned with the driver shaft 110, for example, to align an empty screw passage 176 with the driver 110 when the screwdriver apparatus 100, 100' is used as a drill with a drill tool (as described further below).

With reference again to FIG. 5, when the handle grip 114 moves the loading handle 116 in the distal direction, it moves the driver 110 to engage the tool 111. The tool 111 then moves distally to engage the screw 102, which is pushed first through the screw cartridge body 174 of the screw cartridge 106, then into the screw holder bushing 108. The screw 102 is tapped into the bone (or other target substrate) as it emerges from the distal end of the screw holder bushing 108.

As shown in FIG. 6, the screw cartridge body 174 of the screw cartridge 106 has indexing structures in the form of longitudinal axial channels 182 and oblique channels 84, which are slots on the cylindrical outer profile of the screw cartridge body 174 that are designed to maintain the rotational alignment of the screw cartridge body 174 and cause it to rotate one pitch (one stop) of the rotation of the screw cartridge body 174 during each distal and proximal movement of the handle grip 114. One pitch rotation means rotating the screw cartridge body 174 to align the driver 110 from one of the screw passages 176 in the screw cartridge body 174 to the next. In this manner, the screw cartridge body 174 can be incrementally clocked to each screw position to enable each of the screws 102 to be readily discharged from the screwdriver apparatus 100, 100'.

With reference again to FIG. 5, the handle grip 114 includes a screw cartridge driver 160 that is arranged to interact with the screw cartridge 106 to advance the screw cartridge 106 to the next one of the plurality of incremental rotational positions as the handle grip 114 is displaced fore and aft during use. More particularly, the screw cartridge driver 160 is configured to interact with the aforementioned indexing structures on the outer circumferential profile of the screw cartridge body 174 of the screw cartridge 106 to advance the screw cartridge 106 to the next one of the plurality of incremental rotational positions as the handle grip 114 is displaced fore and aft during use. The indexing structures on the outer circumferential profile of the screw cartridge body 174 of the screw cartridge 106 may comprise an array of sets of intersecting channels, wherein each set of intersecting channels in the array includes one of the longitudinal axial channels 182 of varying depth and one of the oblique channels 184 that extends from a distal leading end of the screw cartridge 106 to a mid-section of the longitudinal axial channel 182. During advancement of the handle grip 114 to a forward position, an indexing structure (i.e., plunger 162) of the screw cartridge driver 160 extends beyond a terminal end of the longitudinal axial channel 182 of one of the sets of intersecting channels in the array and enters the oblique channel 184 of an adjacent one of the sets of intersecting channels, and, during retraction of the handle grip 114 to an aft position, the indexing structure (i.e., plunger 162) of the screw cartridge driver 160 rides in the oblique channel 184 and drives rotation of the screw cartridge 106 to the next one of the plurality of incremental rotational positions. The indexing structure of the screw cartridge driver 160 may be a plunger 162 (e.g., a spring and/or magnetic biased plunger) that extends radially inward toward a central rotational axis of the screw cartridge 106.

In one embodiment, each axial channel 182 has a depth on the proximal side of the outer cylindrical profile of the screw cartridge body 174 of about 0.5 mm and gradually diminishes from the proximal side to a zero depth where the axial channel 182 ends a short distance (about 1.5 mm) prior to reaching the distal side of the outer cylindrical profile of the screw cartridge body 174. Each oblique channel 184 has a depth of about 0.5 mm and starts at the distal side of the outer cylindrical profile of the screw cartridge body 174, directly distal to the end of one of the axial channels 182, and runs proximally therefrom at about a 40-degree angle from the body axis until merging with the adjacent axial channel 182 about 2.5 mm from the proximal side of the outer cylindrical profile of the screw cartridge body 174. The aforementioned channels and dimensions are examples of indexing structures that may be used to assist in rotating the screw cartridge 106.

The rotation of the screw cartridge 106 is described in more detail in the following process. When the handle grip 114 is moved distally, it engages and moves the screw cartridge driver 160 distally to pass over the outer cylindrical profile of the screw cartridge body 174. The screw cartridge plunger 162 is connected to the distal end of the screw cartridge driver 160 and is directed inwardly towards the outer cylindrical profile of the screw cartridge body 174. Prior to the distal movement of the handle grip 114, the tip of the screw cartridge plunger 162 lies within the axial channel 182 and provides rotational alignment of the screw cartridge body 174 of the screw cartridge 106. As the screw cartridge driver 160 passes over the outer cylindrical profile of the screw cartridge body 174, the screw cartridge plunger 162 follows the axial channel 182 until that channel 182 ends and the screw cartridge plunger 162 travels beyond the distal side of the outer cylindrical profile of the screw cartridge body 174. After the screw 102 is inserted (or hole drilled), as the screw cartridge plunger 162 meets the distal side of the cylindrical surface, it engages with the oblique channel 184 and follows the oblique channel 184 until it merges with the adjacent axial channel 182. As the screw cartridge plunger 162 moves proximally through the oblique channel 184, pressure exerted by the screw cartridge plunger 162 on the oblique channel 184 causes the screw cartridge body 174 of the screw cartridge 106 to rotate one pitch. During rotation of the screw cartridge body 174 of the screw cartridge 106, the radial indicators 180 move along a radial indicator channel 186, which shown in FIG. 5.

With reference again to FIGS. 1 through 4, the control element 120 (e.g., switch or switches) located on the top of the handle grip 114 may allow the operator to switch the drive motor 130 rotation direction from clockwise to counterclockwise. For example, in some instances, when the operator pushes forward on the control element 120 or pushes a forward switch or button thereof, the screwdriver apparatus 100, 100' taps/tightens the screw 102 into the bone (or other target substrate) and when the operator pushes backward on the control element 120 or pushes a forward switch or button thereof, the screwdriver apparatus 100, 100' opens the screw from the bone (or other target substrate).

In accordance with aspects of the disclosed embodiments, the screwdriver apparatuses 100, 100' described herein solve problems associated with prior art screwdriver devices by providing an apparatus 100, 100' that autoloads screws 102 from a screw cartridge 106 that is mechanically revolved when the handle grip 114 is actuated by the user, and by utilizing a rotational driving motion that the user directly controls via the control element 120.

According to the example embodiments of the screwdriver apparatuses 100, 100' shown in FIGS. 1 through 4, the screwdriver apparatuses 100, 100' may have a substantially linear form factor that can be held and operated conveniently with one hand. In other instances, it is appreciated that the screwdriver apparatuses may take on a variety of other form factors, such as, for example, a pistol configuration.

According to the example embodiments of the screwdriver apparatuses 100, 100' shown in FIGS. 1 through 4, the screwdriver apparatuses 100, 100' have an ergonomic design that fits in the operator's hand and the operator can easily use it like a marker pen. The base end 122 of the screwdriver apparatus 100 may accommodate a drive motor 130, such as an electric gear motor, for providing rotational motion to the driver 110 during use. The base end 122 of the screwdriver apparatus 100 may further accommodate an onboard battery 132 for powering the drive motor 130 and optionally other components of the screwdriver apparatus 100, such as a control system (not illustrated). In this way, the weight of the drive motor 130 and the battery 132 located at the base end 122 of the screwdriver apparatus 100 be supported by the hand, not the fingers, of the user. This makes the operation more comfortable and easier. The handle grip 114 is located along a length of the screwdriver apparatus 100 in a positon to be manipulated by the user's fingertips. The handle grip 114 is designed so that it may be received and comfortably grasped by the fingertips and may include one or more grip features 115 to assist in preventing the handle grip 114 from sliding from the user's fingertips while in use.

Embodiments of the screwdriver apparatuses 100, 100' described herein may be single-use and disposable. Other embodiments may be multiple use and can be sterilized after use.

According to the example embodiments of FIGS. 1 through 4, the screwdriver apparatuses 100, 100' may be described as electrical, auto-loading screwdrivers that hold screws 102 within a screw cartridge 106 and feed the screws 102 automatically, accurately, flawlessly, fast, and easily into position to be screwed into bone or other target substrates. The illustrated screwdriver apparatuses 100, 100' are cordless and, therefore, need not be connected to an external power source.

In some instances, the screwdriver apparatus 100, 100' utilize for the drive motor 130 a planetary high torque gear-motor that provides adequate torque and speed of rotation for the screwdriver apparatus 100, 100' to be able to tap screws 102 for cranial or orthopedic use into a patient's skull or bones and tighten the screws 102 properly into place. In some instances, the required torque and speed for the screwdriver apparatus 100, 100' may be selectable via an electrical circuit and switch that controls the power current to the drive motor 130. Based on the mechanical formulation, as the operator increases the speed, the torque amount will decrease. The required torque and speed can be selected, for example, based on the operator's knowledge of the patient's age and expected bone strength and structure.

In some instances, the screw cartridge 106 may be rechargeable with additional screws 102. In other instances, the screw cartridge 106 is not intended to be rechargeable, i.e., the screw cartridge 106 may be disposable. In such instances, the screw cartridge 106 may be supplied in a sterilized package and when the operation is done, or the operator needs more screws 102 to use, the screw cartridge 106 will be disposed. In some embodiments, the screws 102 may be arranged in a circular pattern within the screw cartridge 106 in a manner that allows the user to load the screws onto the driver 110 for driving the screws 102 one by one and push them into a screw holder bushing 108 at the working end 112 of the screwdriver apparatus 100 for tapping each screw into the bone as desired.

With reference to FIG. 6, the screws 102 may be distributed in a screw holder cap 170. The screw holder cap 170 may be made of polypropylene or a similar flexible, semi-soft plastic material. In some instances, different variations of the screw holder cap 170 may be provided, each to hold a different type or size of screw 102. In this manner, the operator can select different screw holder caps 170 (and associated different types and sizes of screws 102) for an operation from the different types and sizes of screws 102 that may be used in the medical field. Different embodiments of the screw holder cap 170 (and compatibly configured screw cartridge body 174) may hold different numbers of screws 102 per screw holder cap 170. The screw holder cap 170 with associated screws 102 is preferably distributed in sterile packaging, but in a variation, the screw holder cap 170 and screws 102 can be sterilized locally prior to use.

In some instances, the screws 102 may not be preloaded into the screw holder cap 170. Instead, the screws may be loaded locally by the operator. In some instances, screws in excess of the holes in the screw holder cap 170 may be distributed in sterilized packaging (or they can be sterilized locally) in case a procedure requires a greater number of screws 102 than would fit in the screw holder cap 170.

Before an operation begins, the operator may select the proper sterilized packaged screw cartridge 106 and place it within the cartridge-receiving cavity 107 of the housing or body 104 of the screwdriver apparatus 100, 100' by passing one or more radial indicators 180 on the screw cartridge 106 through a corresponding radial indicator slot 181 which may be provided on the housing or body 104 of the screwdriver apparatus 100, 100'. This simple process is the way that screws 106 may be loaded into the screwdriver apparatus 100, 100'. As further described below, during insertion of the screw cartridge 106 into the screwdriver apparatus 100, 100', the screw cartridge 106 is configured to maintain its alignment with the driver 110 throughout clocked rotation thereof because the radial indicators 180 on the screw cartridge 106 will set the alignment of the first screw at the time of loading.

Although the illustrated embodiment of the screw cartridge 106 is shown as an assembly including the screw holder cap 170 and a separate screw cartridge body 174, in other instances, the screw cartridge 106 may be provided without a screw holder cap 170, and the screws 106 may be placed directly in the screw cartridge body 174.

With reference to the embodiment illustrated in FIGS. 1, 2 and 5, the screwdriver apparatus 100 may be configured with a tool cartridge 150 for holding selectable tools 111. The tools 111 may include screw driver tools available in the market with shape (flat, philips, etc.) and size corresponding to the shape and size of the screw heads known in the market. As shown in the illustrated embodiment, the tools 111 are selectable and located in a circular pattern or array. In some instances, the tool cartridge 150 may be formed in whole or part of a transparent material, so that the tool aligned with the driver 110 can be easily seen by the operator after the tool cartridge 150 is inserted into the screwdriver apparatus 100. The housing or body 104 of the screwdriver apparatus 100 may also be transparent adjacent to the location of the tool cartridge 150, so that the tool aligned with the driver 110 can be easily seen by the operator through the housing or body 104 after the tool cartridge 150 in inserted into the screwdriver apparatus 100. In some instances, the screwdriver apparatus 100 may be considered a universal screwdriver because it may be configured to hold multiple screw driving tools. Typically, the operator selects a desired tool 111 based on the screws 102 selected before the operation starts. After the tool 111 is engaged by the driver 110 as the user manipulates the handle grip 114, the tool 111 moves distally to engage with a screw 102 within the screw cartridge 106 and then continues through the screw holding bushing 108 as previously described.

In some instances, the screw cartridge 106 may be selectable from a choice of screw cartridges 106 according to the desires of the operator and loadable by the operator into the screwdriver apparatus 100, 100'. However, in a variation of the screwdriver apparatus 100, 100', the screw cartridge 106 may be pre-installed when manufactured or at another point in the supply chain, so that operator loading features can be omitted and the operator may immediately use the screwdriver apparatus 100, 100' without selecting and loading the screw cartridge 106.

Various example materials can be used for components of the screwdriver apparatuses 100, 100' disclosed herein. For example, the housing or base 104, the tool cartridge 150, the screw cartridge body 174, and the screw cartridge driver 160 may be made of polyetherimide, for example, Ultem® brand polyetherimide. The power transmission gears 135, 136, 137 and the screw holder bushing 108 may be made of polyetheretherketone. The driver 110, the loading handle 116, the tools 111, and the screw cartridge plunger 162 may be made of stainless steel 304. The screw holder cap 170 may be made of polypropylene. The handle grip 114 may be made of silicone. Other materials are also suitable.

Additional operation of the screwdriver apparatus 100, 100' will now briefly be described in the context of a surgical procedure. During an example operation, the surgeon places the working end 112 of the screwdriver apparatus 100, 100' at a hole in a surgical plate requiring the screw 102. The operator then pushes the handle grip 114 of the screwdriver apparatus 100, 100' distally, which pushes the driver 110 (or driver 110 fitted with a tool 111) through the screw 102 that is located in the screw cartridge 106 toward the surgical plate and underlying bone structure. The driver 110 will engage the screw 102 (directly or indirectly via an intermediate tool 111) and take it to the final place out of the screw holder bushing 108 at the working end 112 of the screwdriver apparatus 100, 100'.

As shown in FIGS. 1 through 4, the control element 120 may be provided on the top of the handle grip 114 such that the operator can use it to turn the drive motor 130 on in a forward direction to tap/tighten the screw 102 or in a backwards direction to open the screw 102 if it had already been applied.

According to the illustrated embodiments, the handle grip 114 is connected to a loading handle 116. Thus, when the operator pushes the handle grip 114 distally to the working end 112, it moves the loading handle 116 distally. The loading handle 116 is connected to the driver 110, resulting in the driver 110 also moving distally. The driver 110 passes into the tool cartridge 150 (when provided) where it engages with a tool 111 pre-selected by the operator via rotation of the tool cartridge 150 to align the desired tool with the path of the driver 110.

The handle grip 114 is also connected to a screw cartridge driver 160 which is configured with a plunger 162 that projects radially inward at its distal end. As the plunger 162 is moved distally by the operator (via displacement of the handle grip 114 and screw cartridge driver 160), the plunger 162 engages with an axial channel 182 while moving distally and on the way back (while moving proximally) it engages to an oblique channel 184 of the screw cartridge 106 to rotate the screw cartridge 106 one rotational position. The screw cartridge 106 is held in place within the screwdriver apparatus 100 and rotates around an axial plunger assembly 178. The axial plunger assembly 178 also serves to align the screws 102 with the driver 110.

Again, the starting screw position may be aligned with the driver 110 using one or more radial indicators 180 on the screw cartridge 106, which align with the radial indicator slot 181 on the housing or body 104 of the screwdriver apparatus 100. This ability to fix the starting screw position allows the operator to use the screwdriver apparatus 100 with a drill feature described below or with different types or sizes of screws 102 loaded into the screw cartridge 106.

According to aspects of the present disclosure, an operator may place the distal end of the screw holder bushing 108 against the bone (or other target substrate) to start the tapping process. Because there is no gap between the screw holder bushing 108 at its distal end and the bone in this manner, the screw 102 cannot be dropped before engaging therewith. In some instances, the tool mating interface on the head of the screw 102 and the screw mating interface on the driver 110 or tool 111 may dimensionally very close, creating a tight mechanical bond when the driver 110 or tool 111 engages the screw 102.

In some instances, an inner diameter of the screw holder bushing 108 and the head of the screw 102 may be configured to be in interference fit tolerance, so that a longitudinal axis of the screw 102 remains parallel to a longitudinal axis of the screwdriver apparatus 100 as the screw 102 passes through the screw holder bushing 108 and is secured to the bone in that orientation, preventing a screw drop.

The screw holder bushing 108 may be removable by the operator, so it can be separately sterilized, if needed or desired. Alternatively, the operator can replace it with a disposable, single-use variation that is pre-sterilized or locally sterilized. In some instances, a variety of configurations of screw holder bushings 108 may be available for the screwdriver apparatus 100, each with a different internal channel diameter corresponding to different screw head diameters available in the market. Prior to an operation, the operator can insert the screw holder bushing of the desired size into the screwdriver apparatus 100 to match the desired screw head size. In some embodiments, the screw holder bushing 108 may be made of polycarbonate plastic, nylon 6/6 plastic, or other suitable material.

In some instances, the screwdriver apparatus 100 shown in FIGS. 1 and 2 may be used as a drill to make, for example, pilot holes during an operation. In such instances, one or more drill tools can be placed in the tool cartridge 150 (along with or exclusive of driver tools). In some cases, the operator can select from a variety of tool cartridges 150, each of which will accommodate drill tools with different diameters and head types.

The operator can set the screwdriver apparatus 100 to drill by selecting the drill tool and by selectively increasing an operational speed of the drive motor 130, such as, by engaging a user manipulable control for that purpose. When the operator wishes to use the screwdriver apparatus 100 as a drill, the operator may use it without the screw cartridge 106 installed or with a specially configured screw cartridge 106 that leaves one or more positions of the screw cartridge 106 open for drill use, or where at least one screw 102 has already been used from the screw cartridge 106. The operator can select a drill tool by loading it into the tool cartridge 150 and loading the tool cartridge 150 into the screwdriver apparatus 100 so that the desired drill tool is aligned with the driver 110 for use.

In some instances, the housing or body 104 and the tool cartridge 150 may have transparent windows so that the operator can observe which tool 111 is aligned with the driver 110. In another embodiment, open areas expose sufficiently the tool 111 or drill tool (not illustrated) to allow the operator to align the desired tool 111 or drill tool with the driver 110.

In some instances, the handle grip 114 and the housing or body 114 may include respective transparent windows and the screw cartridge 106 may be made of sufficiently transparent material to allow the operator to determine more easily the position of the open passage in the tool cartridge 150 to ensure it is aligned with the driver 110 and the drill tool. If the tool cartridge 150 is preloaded with tools, prior to or after using the drill tool, the operator can rotate the tool cartridge 150 to align a different tool 111 with the driver 110 for insertion or removal of a screw 102 by observing the selectable tools through the transparent windows or openings described above.

The tool cartridge 150 may be held in place within the screwdriver apparatus 100 and rotates around an axial plunger 190. The axial plunger 190 of the tool cartridge 150 also serves to align an active position of the tool cartridge 150 with the driver 110.

Besides the advantages already identified, the screwdriver apparatuses 100, 100' described herein have other advantages over the prior art. For instance, using some embodiments of screwdriver apparatus 100, 100' relieves surgeons from the arduous task of loading the screwdriver manually. Embodiments of the screwdriver apparatus 100, 100' eliminate the possibility of dropping and losing screws and prevents the screws from being flung away as is possible with other electrical screwdrivers in use. Embodiments described herein thus make operating more secure, easier, and faster for surgeons and reduce the risks during operations of lost screws and, therefore, significantly lessens risk to the patient.

Again, although certain specific details are set forth in order to provide a thorough understanding of various disclosed embodiments, one skilled in the relevant art will recognize that embodiments may be practiced without one or more of these specific details. Moreover, aspects and features of the various embodiments described above can be combined to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A screw cartridge for a screwdriver apparatus, the screw cartridge comprising:
   a screw cartridge body; and
   a plurality of screws supported within the screw cartridge body to be selectively discharged from the screwdriver apparatus,
   wherein the screw cartridge is configured to be removably received in the screwdriver apparatus to facilitate replacement of the screw cartridge,
   wherein, when the screw cartridge is installed in the screwdriver apparatus for use, the screw cartridge is configured to be selectively advanced to a next one of a plurality of incremental positions via interaction with a displaceable screw cartridge driver of the screwdriver apparatus, and
   wherein the screw cartridge body includes indexing structures on an outer circumferential portion with which the screw cartridge driver interacts to advance the screw cartridge to a next one of the plurality of incremental positions as the screw cartridge driver is displaced fore and aft during use.

2. The screw cartridge of claim 1, wherein the indexing structures on the outer circumferential portion of the screw cartridge body comprise an array of sets of intersecting channels, wherein each set of intersecting channels in the array includes a longitudinal channel of varying depth and an oblique channel extending from a leading end of the screw cartridge to a mid-section of the longitudinal channel.

3. The screw cartridge of claim 2, wherein the indexing structures are arranged such that, during advancement of the screw cartridge driver to a forward position, an indexing structure of the screw cartridge driver extends beyond a terminal end of the longitudinal channel of one of the sets of intersecting channels in the array and enters the oblique channel of an adjacent one of the sets of intersecting channels, and, during retraction of the screw cartridge driver to an aft position, the indexing structure of the screw cartridge driver rides in the oblique channel and drives rotation of the screw cartridge to a next one of the plurality of incremental positions.

4. The screw cartridge of claim 1, wherein the screw cartridge further comprises a screw holder cap including a plurality of screw receiving apertures in which the plurality of screws are receiveably held.

5. The screw cartridge of claim 4, wherein the screw holder cap is coupled to the screw cartridge body, and where the screw cartridge body includes a plurality of screw passages through each of which a respective one of the screws held by the screw holder cap is positioned.

6. The screw cartridge of claim 1, wherein the screw cartridge further comprises an axial plunger assembly configured to enable the screw cartridge to be removably received by a base of the screwdriver apparatus.

7. The screw cartridge of claim 1, wherein the screw cartridge includes one or more indicators on a side thereof to facilitate loading of the screw cartridge in proper working alignment within the screwdriver apparatus.

8. The screw cartridge of claim 7, wherein the one or more indicators comprise a plurality of projections formed integrally with the screw cartridge body in linear alignment with each other.

9. A screwdriver apparatus, comprising:
   a base;
   a screw cartridge driver; and
   a screw cartridge removably receivable in the base, the screw cartridge including a screw cartridge body and a plurality of screws supported within the screw cartridge body to be selectively discharged from the screwdriver apparatus,
   wherein, when the screw cartridge is installed in the base for use, the screw cartridge is configured to be selectively advanced to a next one of a plurality of incremental positions via interaction with the screw cartridge driver, and
   wherein the screw cartridge body includes indexing structures on an outer circumferential portion with which the screw cartridge driver interacts to advance the screw cartridge to the next one of the plurality of incremental positions as the screw cartridge driver is displaced fore and aft during use.

10. The screwdriver apparatus of claim 9, wherein the screw cartridge driver includes an indexing structure in the form of a plunger that extends radially inward toward a central rotational axis of the screw cartridge.

11. The screwdriver apparatus of claim 9, further comprising:
a handle grip movably coupled to the base and configured to be manually displaced in a longitudinal direction by a user toward a working end of the screwdriver apparatus to move a driver into engagement with one of the plurality of screws of the screw cartridge and to displace the screw to the working end of the screwdriver apparatus for presenting the screw to be screwed into a target substrate.

12. The screwdriver apparatus of claim 11, wherein the screw cartridge driver is arranged to interact with the screw cartridge to advance the screw cartridge to a next one of the plurality of incremental positions as the handle grip is displaced fore and aft during use.

13. The screwdriver apparatus of claim 11, further comprising:
a control element manipulable by a user to activate rotational movement of a driver to drive the screw into the target substrate, and
wherein the displacement of the handle grip and the screw toward the working end of the screwdriver apparatus is able to be carried out independent of manipulation of the control element to activate rotational movement of the driver.

14. The screwdriver apparatus of claim 13, wherein the control element is carried by the handle grip for manipulation by the user on the handle grip.

15. The screwdriver apparatus of claim 11, further comprising:
the driver;
a drive motor; and
a plurality of mechanical power transmission components coupled between the drive motor and the driver to transfer rotational motion of the drive motor to the driver during use.

16. The screwdriver apparatus of claim 9, wherein the base includes a screw cartridge-receiving cavity on a lower side thereof for insertably receiving the screw cartridge.

17. A screwdriver apparatus, comprising:
a base;
a driver;
a drive motor;
a screw cartridge driver;
a screw cartridge removably receivable in the base, the screw cartridge including a screw cartridge body and a plurality of screws supported within the screw cartridge body to be selectively discharged from the screwdriver apparatus;
a handle grip movably coupled to the base and configured to be manually displaced in a longitudinal direction by a user toward a working end of the screwdriver apparatus to move the driver into engagement with one of the plurality of screws of the screw cartridge and to displace the screw to the working end of the screwdriver apparatus for presenting the screw to be screwed into a target substrate; and
a plurality of mechanical power transmission components coupled between the drive motor and the driver to transfer rotational motion of the drive motor to the driver during use,
wherein, when the screw cartridge is installed in the base for use, the screw cartridge is configured to be selectively advanced to a next one of a plurality of incremental positions via interaction with the screw cartridge driver, and
wherein the plurality of mechanical power transmission components includes a driver gear coupled to an output of the drive motor, a pinion gear coupled to the driver, and an intermediate gear meshed with both of the driver gear and the pinion gear, the intermediate gear including elongated teeth enabling the pinion gear to slide longitudinally back and forth along a length of the intermediate gear during displacement of the handle grip and driver during use of the screwdriver apparatus.

18. A screwdriver apparatus, comprising:
a base;
a driver;
a drive motor;
a screw cartridge driver;
a screw cartridge removably receivable in the base, the screw cartridge including a screw cartridge body and a plurality of screws supported within the screw cartridge body to be selectively discharged from the screwdriver apparatus;
a handle grip movably coupled to the base and configured to be manually displaced in a longitudinal direction by a user toward a working end of the screwdriver apparatus to move the driver into engagement with one of the plurality of screws of the screw cartridge and to displace the screw to the working end of the screwdriver apparatus for presenting the screw to be screwed into a target substrate; and
a plurality of mechanical power transmission components coupled between the drive motor and the driver to transfer rotational motion of the drive motor to the driver during use,
wherein, when the screw cartridge is installed in the base for use, the screw cartridge is configured to be selectively advanced to a next one of a plurality of incremental positions via interaction with the screw cartridge driver, and
wherein the driver is part of a driver assembly, and wherein the driver assembly includes a return spring to bias the driver toward an aft position to enable the driver to return from an advanced position to the aft position under the bias of the return spring.

19. The screwdriver apparatus of claim 18, wherein the bias of the return spring assists in rotating the screw cartridge to a next one of the plurality of incremental positions as the driver retreats to the aft position.

* * * * *